US012746385B2

(12) United States Patent
Ye et al.

(10) Patent No.: US 12,746,385 B2
(45) Date of Patent: Sep. 29, 2026

(54) WRIST-WORN NERVE STIMULATOR AND USE METHOD THEREFOR

(71) Applicants: Hangzhou Fasikl Technology Co., Ltd., Hangzhou (CN); Fasikl Incorporated, Dallas, TX (US)

(72) Inventors: Bing Ye, Hangzhou (CN); Baitong Wang, Hangzhou (CN); Jules Anh Tuan Nguyen, Dallas, TX (US); Zhen Zhang, Hangzhou (CN)

( * ) Notice: Subject to any disclaimer, the term of this patent is extended or adjusted under 35 U.S.C. 154(b) by 430 days.

(21) Appl. No.: 18/335,121

(22) Filed: Jun. 14, 2023

(65) Prior Publication Data

US 2023/0321430 A1 Oct. 12, 2023

(51) Int. Cl.
*A61N 1/04* (2006.01)

(52) U.S. Cl.
CPC ......... *A61N 1/0484* (2013.01); *A61N 1/0456* (2013.01); *A61N 1/0496* (2013.01)

(58) Field of Classification Search
CPC .. A61N 1/0456; A61N 1/0492; A61N 1/0484; A61N 1/36014
See application file for complete search history.

(56) References Cited

U.S. PATENT DOCUMENTS

2012/0203245 A1 8/2012 Imabayashi et al.
2017/0259061 A1 9/2017 Simon et al.
2018/0250510 A1* 9/2018 Ziv ........................ A61B 5/339
2020/0346008 A1 11/2020 Song

* cited by examiner

*Primary Examiner* — Alyssa M Alter
(74) *Attorney, Agent, or Firm* — Yuhao Liang

(57) ABSTRACT

The present invention relates to the field of wearable neurotherapy devices, and particularly relates to a wrist-worn nerve stimulator. The nerve stimulator is suitable for the wrist and other parts of limbs. For the nerve stimulator, a conducting medium attached to a strap not only ensures no tingling sensation during electrical stimulation therapy, but also alleviates the problem of discomfort without prejudice to the therapeutic effect, thereby reducing the difficulty of assembling the nerve stimulator and improving wearing adaptability; in addition, it can be seen from the use of a first strap and an electrical stimulation part that the wrist-worn nerve stimulator has a split structure and is composed of the first strap and the electrical stimulation part, such that the difficulty of disassembling basic frameworks for electrical stimulation therapy is significantly reduced, and it can be understood that the consumable first strap is easier to be replaced.

8 Claims, 13 Drawing Sheets

WRIST-WORN NERVE STIMULATOR AND USE METHOD THEREFOR

TECHNICAL FIELD

The present invention relates to the field of wrist-worn neurotherapy devices, and particularly relates to a wrist-worn nerve stimulator.

BACKGROUND

Electrical stimulation therapy is a process related to electrolysis, where an electrical current is sent through an electrode to a certain tissue or organ of an organism to achieve the purpose of therapy.

Electrical energy can be delivered transcutaneously with a nerve stimulation system via electrodes on the skin surface to stimulate peripheral nerves, as non-limiting examples, such as the median nerve, radial nerve, and/or ulnar nerve in the upper limbs. Electrical stimulation of these nerves, as shown, provides therapeutic benefits for various diseases, including but not limited to dyskinesia (including but not limited to essential tremor, Parkinson's tremor, postural tremor and multiple sclerosis), urology diseases, gastrointestinal diseases, heart diseases and inflammatory diseases. Trans cutaneous electrical nerve stimulation is a peripheral electrical nerve stimulation therapy technology. Because transcutaneous electrical nerve stimulation has the advantages of being non-traumatic, non-invasive, easy to operate, well tolerated, short-lived, free from side effects and affordable, it has become a hot spot in clinical application research and has been widely applied. The wrist-worn nerve stimulator is a small wearable electrical stimulation device, which can be worn on the wrist, and through a plurality of electrode plates closely attached to a peripheral edge of the wrist and according to certain rules, can stimulate the median nerve, radial nerve and/or ulnar nerve distributed in the hand to achieve the therapeutic effect.

In other words, the current, through an electrode reaction at the electrode/conductive solution interface, converts electrons into ions and transmits them to the organism, and then, the current passes through the tissues and organs and reaches another electrode/conductive solution interface. The electrode reaction on this interface means converting ions into electrons and leaving the organism to enter the electrode.

However, an electrode plate is an electrode generally made of metal materials, and a metal electrode plate is hard and brings poor comfort to a wearer when exposed to the skin of the wrist. In this case, disposable conductive paste or conductive solution is usually supplemented to reduce the resistance of contact with human skin, so as to achieve better therapeutic effects. However, the way of applying the conductive paste or conductive solution might increase the difficulty of operation and cause discomfort to the wearer, while lack of the conductive paste or conductive solution might cause a tingling sensation in the area; The retrieved patent document 1 requires the wrist to be applied with the conductive paste or conductive solution.

Patent document 1 discloses a Chinese invention patent with the application number of 202210337333.8, entitled "Wrist-worn nerve stimulator suitable for both left and right hands and use method therefor.

SUMMARY

In order to solve the above problems, the present invention provides a wrist-worn nerve stimulator that eliminates the need to apply conductive paste and solves the problem of discomfort caused by applying.

To achieve the above objective, the present invention uses a technical solution as follows:

A wrist-worn nerve stimulator, including an electrical stimulation part and a first strap, where after the first strap is worn on the wrist, the electrical stimulation part is superimposed on the first strap to keep an output end of the electrical stimulation part contactable with a conducting medium on the first strap, the conducting medium is solid-state, at least two surfaces of the conducting medium are exposed outside the constraint of the first strap on the conducting medium, one surface of the conducting medium is pasted on the surface of the wrist in the wearing process, and an output end of the electrical stimulation part is in contact with the other surface of the conducting medium.

The nerve stimulator of the present invention is suitable for wearing on the wrist and other parts of limbs. For the nerve stimulator, the design of a conducting medium attached to a strap not only ensures that a wearer feels no tingling sensation during electrical stimulation therapy, but also alleviates the problem of discomfort caused by applying of conductive paste/solution without prejudice to the therapeutic effect, thereby reducing the difficulty of assembling the nerve stimulator and achieving the goal of improving wearing adaptability; in addition, it can be seen from the use of a first strap and an electrical stimulation part that the wrist-worn nerve stimulator of the present invention has a split structure and is composed of the first strap and the electrical stimulation part, such that the difficulty of disassembling basic frameworks for electrical stimulation therapy is significantly reduced, and it can be understood that the consumable first strap is easier to be replaced.

Figure 1:
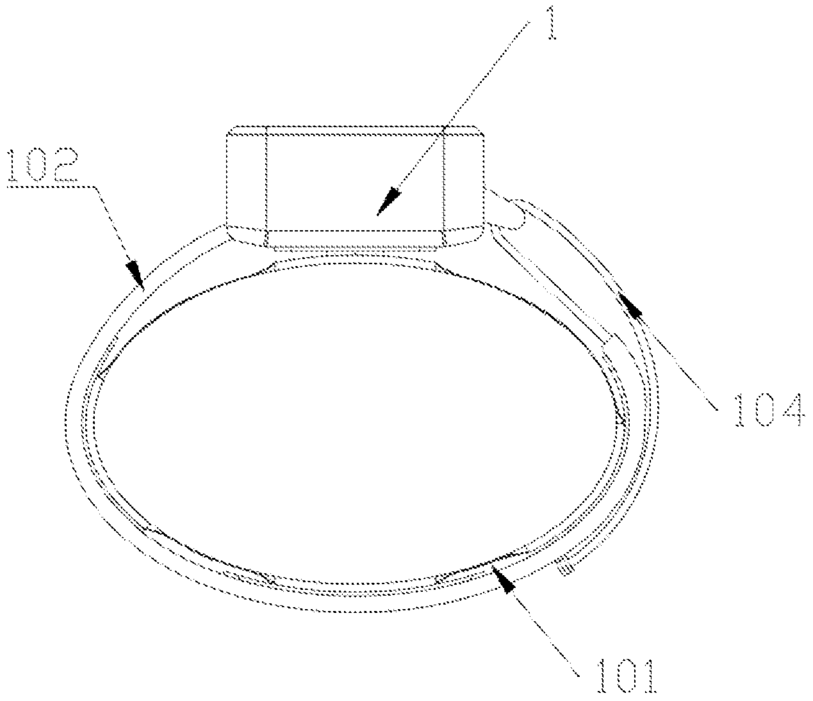
FIG. 1 is a space diagram of the present invention sleeved behind a wrist.

Description of reference numerals: 1, electrical stimulation part; 100, conduction plate; 101, conductive sponge; 102, second strap; 103, convex edge; 104, elastic part; 105, wire; 2, first strap; 3, conducting medium; 4, silver chloride electrode; 5, first release film; 6, second release film; 7, color mark.

DETAILED DESCRIPTION OF THE EMBODIMENTS

To better understand the objective, structure and function of the present invention, a wrist-worn nerve stimulator of the present invention is described in detail below in combination with the accompanying drawings.

Figure 2:
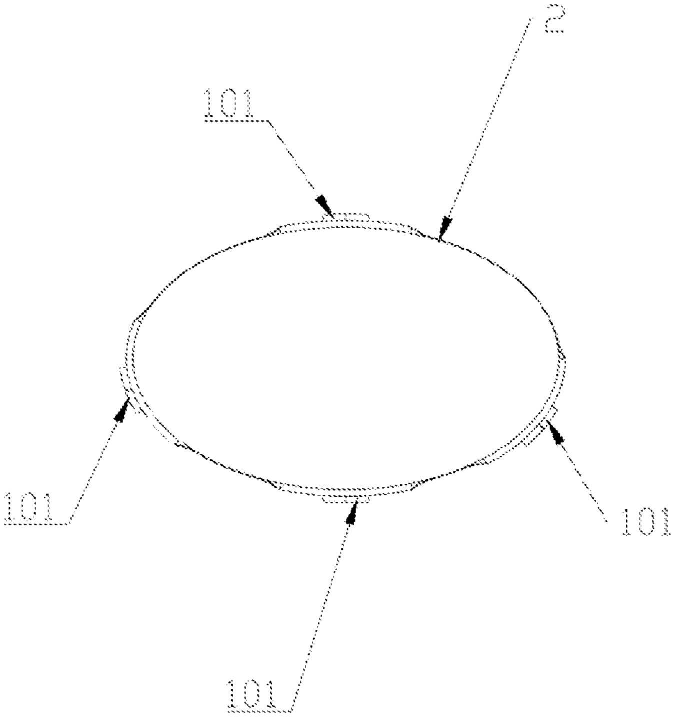
FIG. 2 is a space diagram of a first strap of the present invention sleeved behind the wrist.
Figure 3:
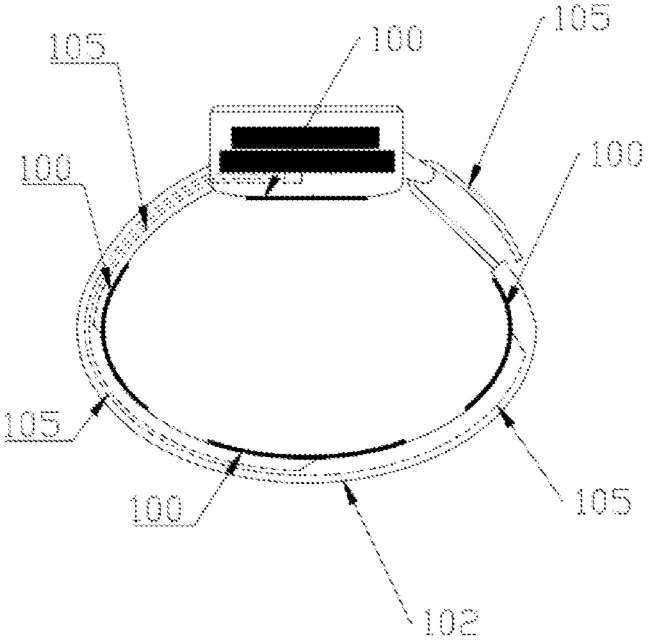
FIG. 3 is a space diagram of an electrical stimulation part.
Figure 4:
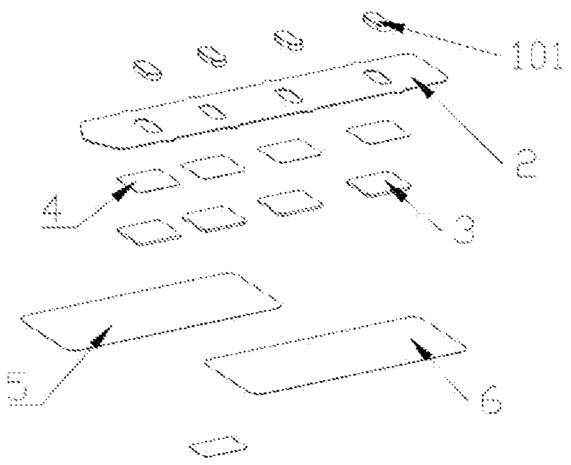
FIG. 4 is a schematic diagram of explosion of the first strap.
Figure 5:
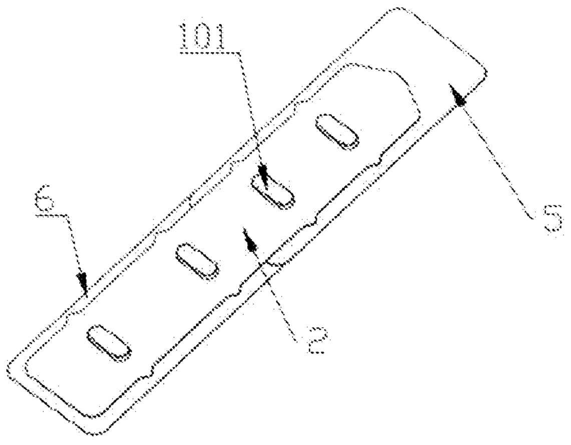
FIG. 5 is a space diagram of the first strap.
Figure 6:
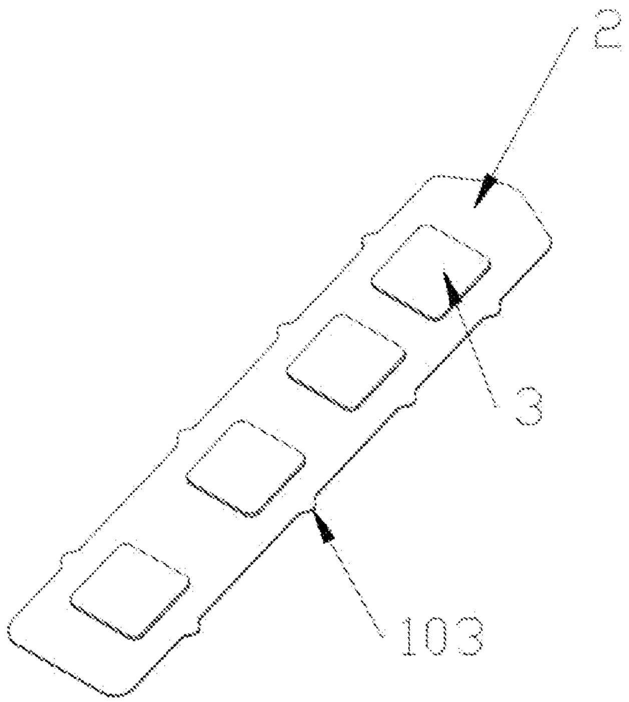
FIG. 6 is a space diagram of the other view surface after removing a release film from the first strap.
Figure 7:
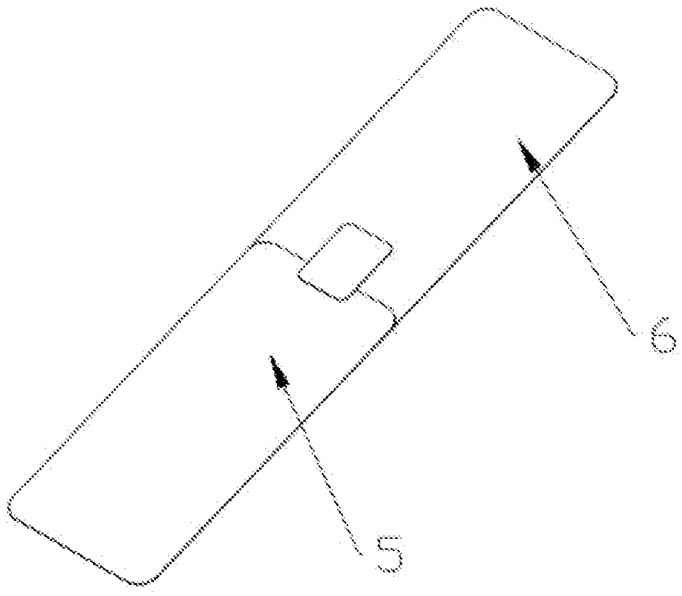
FIG. 7 is another view of FIG. 5.

As shown in FIGS. 1-7, the wrist-worn nerve stimulator of the present invention includes an electrical stimulation part 1 and a first strap 2, where a conducting medium 3 and a first conductive component fitted with the conducting medium 3 are pasted on the first strap 2, the conducting medium 3 and the first conductive component are respectively arranged on two opposite surfaces of the first strap 2; in other words, at least two surfaces of the conducting medium 3 are exposed outside the constraint of the first strap 2 on the conducting medium 3, the electrical stimulation part 1 and the first strap 2 both have an elongated structure and are worn on the wrist in an orderly and superimposed manner: one surface of the first strap 2 where there is the conducting medium 3 is fitted onto a therapy site and the strap is worn on the wrist, the electrical stimulation part 1 is worn on the first strap 2, and a conduction plate 100 of the electrical stimulation part 1 corresponds to the first conductive component; and During the electrical stimulation therapy, the current sequentially passes through the conduction plate 100, the first conductive component and the conducting medium 3 from the electrical stimulation part 1, and then enters the patient's skin, to stimulate peripheral nerves under the skin, including but not limited to the median nerve, radial nerve and/or ulnar nerve in the upper limb.

It can be seen therefrom that the use of the first strap 2 with the accompanying conducting medium 3 enables a mild and painless therapy, where the current, despite very little energy, is automatically sent to the excitable tissues of the organism through an electrode/electrolyte solution interface, which eliminates the need to apply the conductive paste/solution, improves convenience, reduces energy consumption, and improves therapeutic effects and wearing comfort.

The conduction plate 100 and the first conductive component constitute an output end of the electrical stimulation part 1, so the output end of the electrical stimulation part 1 has a split structure; the first conductive component is arranged on the first strap 2 to improve the assembly success rate, and after the first conductive component is arranged on the first strap 2, setting positions therebetween can be distinguished based on the changes in the thickness, therefore, during assembly, the position of the first conductive component can be easily identified, such that quick correspondence between the first conductive component and the conduction plate 100 can be achieved.

Specifically, a silver chloride electrode 4 is arranged between the first conductive component and the conducting medium 3, and the silver chloride electrode 4 is coated with a silver chloride coating on a PE conductive film, such that in case of a relatively small current, the silver chloride electrode 4 almost becomes a non-polarized electrode, which not only has the performance of not being easily polarized, but also generates smaller electrical noise.

The PE film is composed of 55% PE material and 45% conductive carbon black.

It can be seen from the wearing of the electrical stimulation part 1 and the first strap 2 that the electrical stimulation part 1 and the first strap 2 are worn in a two-step manner. The purpose is to make the patients with hand tremors also able to wear alone, which facilitates operation and also replacement of the first strap 2 (in specific embodiments, the first strap 2 is a medical adhesive tape fixed on the wrist and belongs to the consumable scope).

In addition, pressure-sensitive adhesive or silicon gel arranged on the bottom surface of the medical adhesive tape is used to be pasted on the wrist, to keep a mobile adhesive tape on the wrist.

Also, a plurality of air holes are formed on the medical adhesive tape to divert heat under the medical adhesive tape and improve the patient's comfort.

The first conductive component on the medical adhesive tape is a conductive sponge 101 protruding towards the direction of the electrical stimulation part 1. In this embodiment, there are four conductive sponges 101. In the wearing process, the conductive sponge 101 will be compressed and deformed, which can ensure the stability of current flow and reduce discomfort caused by use of metal.

It should be noted that the conductive sponge 101 is mainly composed of 1.5%-3% acrylic adhesive, 0.5%-1% polyester resin, 1%-1.5% thermoplastic polyurethane, 2.5%-5% polyester fiber, 1%-2% copper, 85%-90% polyester sponge and 1%-1.5% nickel. At this composition ratio, the conductive sponge 101 produced has excellent conductivity and ductility.

In this embodiment, the conducting medium 3 is hydrogel, which, in the form of an array, is distributed on the medical adhesive tape, is soft with water as a dispersion medium, and is capable to maintain a certain shape and absorb a large amount of water, therefore, it can be arranged behind the medical adhesive tape to realize the electrical current conduction.

Of course, the hydrogel has a certain viscosity, and in order to prevent scrapping due to adhesion between the hydrogels caused by any error in the wearing process, a release film is covered on the hydrogel, and the release film is made of a transparent plastic material, which further reduces the probability of operating errors;

further, the release films refer to a first release film 5 and a second release film 6 respectively, specifically, before using, any first release film 5 is removed first, and after wearing thereof is completed, the second release film 6 is removed, such that the corresponding hydrogel is fitted on the wrist; the first release film 5 and the second release film 6 described herein can cover a plurality of hydrogels at the same time or a single hydrogel, the specific selection method depends on the current model, and the above is only a specific description. A second strap 102 is arranged on a side surface of the electrical stimulation part 1, the output end of the electrical stimulation part 1 is the conduction plate 100 made of conductive silicone rubber, the conduction plate 100 is arranged at the bottom of the electrical stimulation part 1 and on an inner side of the second strap 102, the second strap 102 is made of silicone rubber or formed by TPU injection molding, and the formed second strap 102 can be bent and deformed to better fit the wrist; and in addition, a buckle is arranged on the side surface of the electrical stimulation part, and a tail end of the second strap 102 penetrates the buckle and returns to the surface of the second strap 102, such that a Velcro on an inner surface of the tail end of the second strap 102 is connected with the surface of the second strap 102.

It should be noted that an elastic part 104 is arranged at the tail end of the second strap 102, in the wearing process, the elastic part 104 can be pulled to keep close contact between the electrical stimulation part 1 and the conductive sponge 101, and through a Velcro thereon, the elastic part 104 is pasted on the surface of the other end of the electrical stimulation part 1.

At least one of the conduction plates 100 is used to form a circuit to ensure that the stimulated current can pass through the body part to be treated, and the conduction plate 100 is arranged on the back of the wrist.

A plurality of wires 105 are arranged inside the second strap 102, one end of each wire 105 is connected with the conduction plate 100 and the other end thereof is connected with the electrical stimulation part 1, and the electrical stimulation part 1 is a prior art, so its structure will not be further elaborated.

In order to further facilitate the observation of the correspondence between the conductive sponge 101 and the conduction plate 100, indication marks are arranged on the side surface of the second strap 102 and on the outer edge of the medical adhesive tape, these indication marks correspond to the center positions of the conduction plate 100 and the conductive sponge 101, respectively, and through observation of the indication marks on the second strap 102 and the medical adhesive tape, the correspondence between the conduction plate 100 and the conductive sponge 101 can be obtained in the overlapped area, so as to make adjustments in a timely manner.

Specifically, the indication mark on the second strap 102 is a color mark 7, while the indication mark on the first strap 2 is a convex edge 103, and it is observed whether the color mark 7 is aligned with the convex edge 103.

It should also be noted that the electrical stimulation unit 1 is a host.

Figure 8:
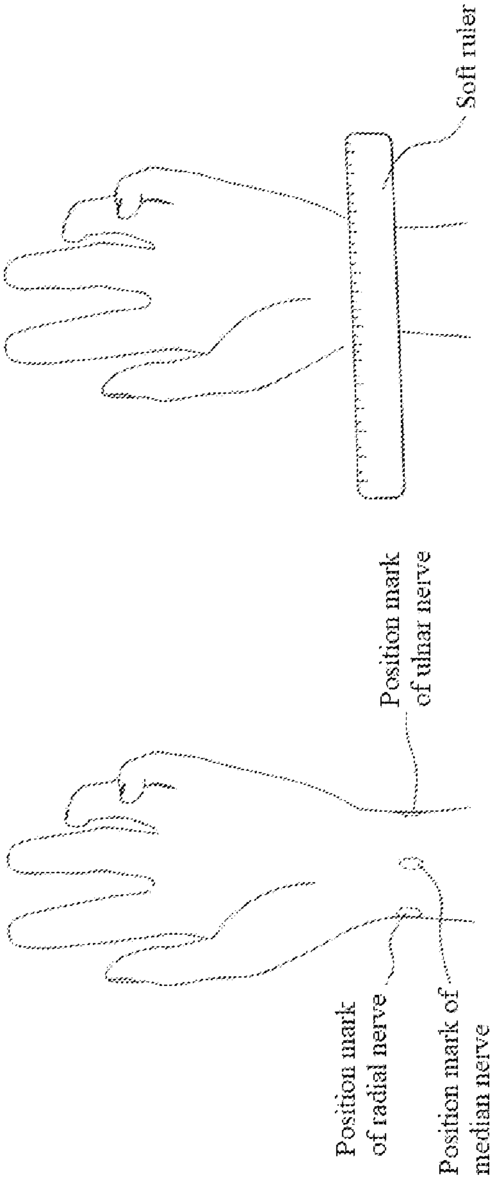
FIG. 8 is a schematic diagram of wearing according to S1 and S2 in a use method of the present invention.
Figure 9:
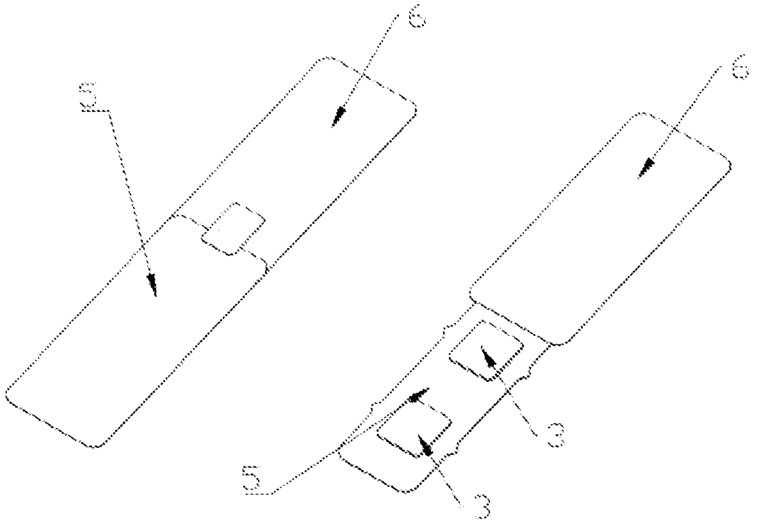
FIG. 9 is a schematic diagram of wearing according to S3 in the use method of the present invention.
Figure 10:
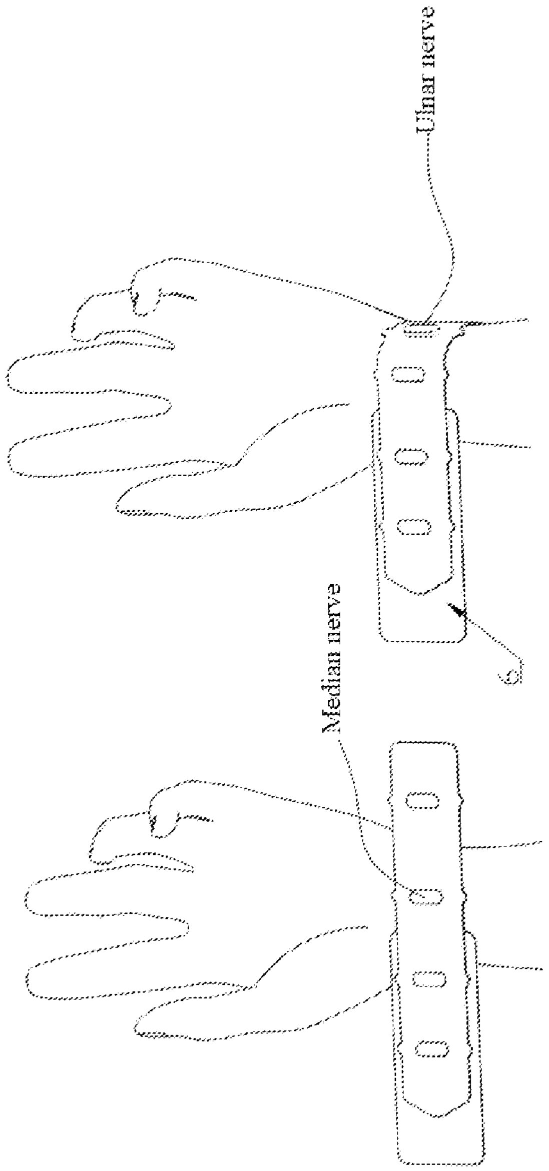
FIG. 10 is a schematic diagram of wearing according to S4 in the use method of the present invention.
Figure 11:
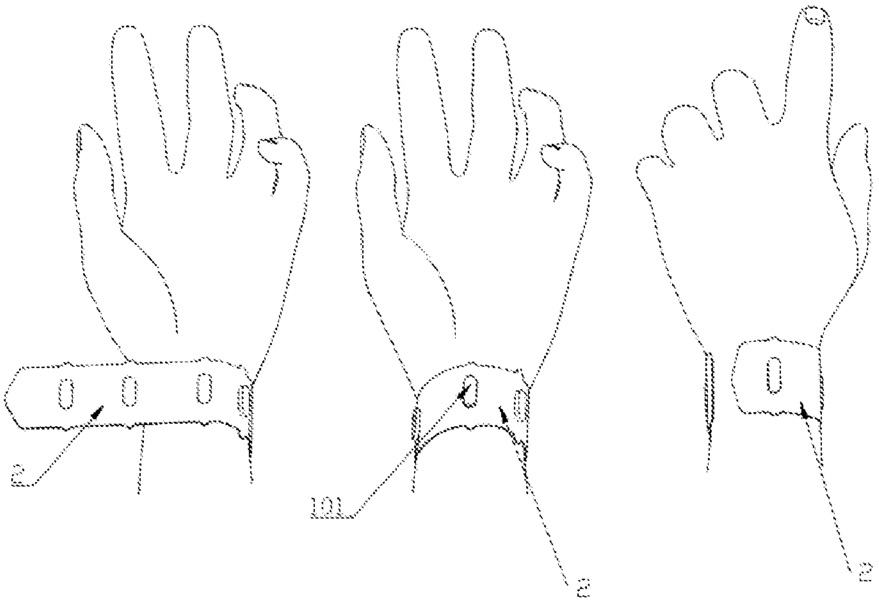
FIG. 11 is a schematic diagram of wearing according to S5 in the use method of the present invention.
Figure 12:
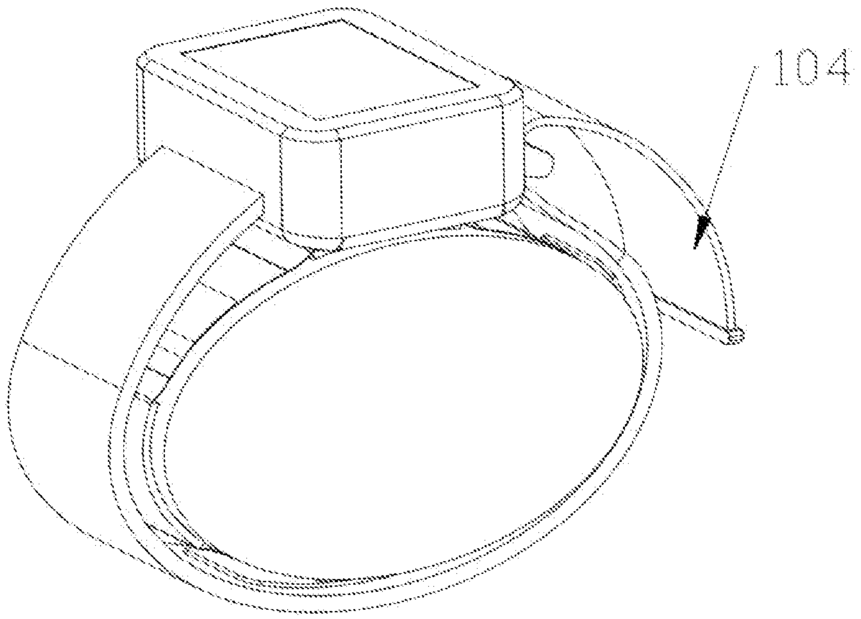
FIG. 12 is a schematic diagram of wearing according to S6 in the use method of the present invention.
Figure 13:
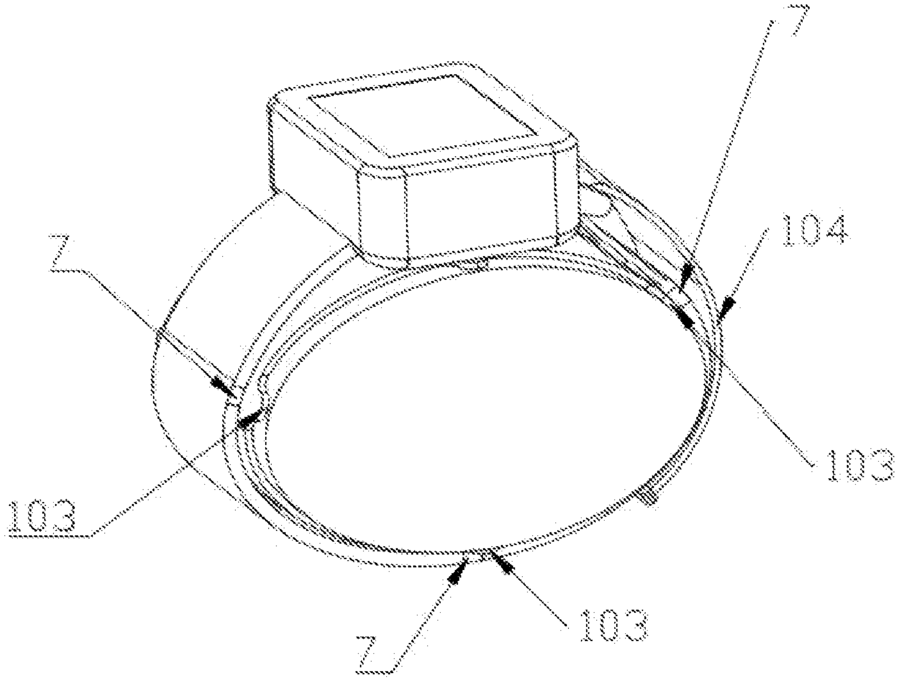
FIG. 13 is a schematic diagram of wearing according to S7 in the use method of the present invention.

As shown in FIGS. 8-13, a method for using the wrist-worn nerve stimulator includes the following steps:

S1, according to the instructions of wrist nerve anatomy, the nearest position of a nerve (such as the median nerve, radial nerve or ulnar nerve) in the wrist corresponding to the wrist surface is found, and marking on the skin surface is performed after finding thereof;

S2, the marked position is measured with a soft ruler, relative distances between the median nerve, radial nerve and ulnar nerve are recorded, the size of the wrist is measured with a soft ruler, and comparison of the second straps 102 of a plurality of models is made according to the recorded relative distances and wrist size, to select the most appropriate model;

S3, the first release film 5 is torn by hand to expose the hydrogel corresponding to the median nerve and the ulnar nerve;

S4, the hydrogel is pasted onto the corresponding nerve of the wrist, such that an electrode plate composed of the conduction plate 100 and the conductive sponge 101 can correspond to the median nerve and the ulnar nerve respectively;

S5, the second release film 6 is torn off to expose the hydrogel corresponding to the radial nerve and the back of the wrist, the hydrogel corresponding to the radial nerve is pasted on the position of the radial nerve of the wrist, and the hydrogel used for corresponding the back of the wrist is pasted on the back of the wrist;

S6, the elastic part 104 of the second strap 102 is loosened and sleeved on the wrist, the second strap 102 is overlapped on the first strap 2, and the second strap 102 is adjusted, such that the conduction plate 100 overlaps with the wet conductive foam; and S7, after adjustment, the elastic part 104 is tightened and buckled to ensure that the conduction plate 100 is tightly conductive with the conductive sponge 101, it is observed whether the three color marks 7 on the side of the second strap 102 are basically aligned with the corresponding convex edge 103 of the wet electrode strap, in case of an excessive deviation, the second strap 102 and the entire host are adjusted until they are basically aligned, and after adjustment and alignment, the host is turned on to start therapy.

The above implementation modes merely describe the preferred embodiments of the present invention, and are not intended to limit the scope of the present invention. Without departing from the design spirit of the present invention, various modifications and improvements of the technical solution of the present invention made by those of ordinary skill in the art should fall within the scope of protection determined in the claims of the present invention.

The invention claimed is:

1. A wrist-worn nerve stimulator, comprising an electrical stimulation part and a first strap, wherein after the first strap is worn on the wrist, the electrical stimulation part is superimposed on the first strap to keep an output end of the electrical stimulation part contactable with a conducting medium on the first strap, the conducting medium is solid-state, at least two surfaces of the conducting medium are exposed outside a constraint of the first strap on the conducting medium, one surface of the conducting medium is pasted on a surface of the wrist during wearing process, and an output end of the electrical stimulation part is in contact with the other surface of the conducting medium;

wherein a second strap that can be worn on the wrist is arranged on a side surface of the electrical stimulation part, the output end of the electrical stimulation part has a split structure, and comprises a plurality of conduction plates arranged on an inner surface of the second strap and constitute a circuit, and a plurality of first conductive components installed on the first strap and connected with the conducting medium;

the second strap surrounds the first strap, and the conduction plates corresponds to the respective first conductive components; during electrical stimulation therapy, a current from the electrical stimulation part sequentially passes through the corresponding conduction plate, the first conductive component and the conducting medium, and then enters the wrist.

2. The wrist-worn nerve stimulator according to claim 1, wherein the first conductive component is deformed due to compression in the wearing process.

3. The wrist-worn nerve stimulator according to claim 2, wherein corresponding marking indicators are arranged on the outer edges of the second strap and the first strap.

4. The wrist-worn nerve stimulator according to claim 3, wherein a buckle is arranged on the side surface of the electrical stimulation part, and a tail end of the second strap penetrates the buckle and returns to the surface of the second strap, such that a hook and loop fasteners on an inner surface of the tail end of the second strap is connected with the surface of the second strap.

5. The wrist-worn nerve stimulator according to claim 1, wherein the conducting medium is hydrogel.

6. The wrist-worn nerve stimulator according to claim 5, wherein a silver chloride film is arranged between the conducting medium and the first conductive component.

7. The wrist-worn nerve stimulator according to claim 6, wherein a release film is attached to the surface of the conducting medium backward the second strap.

8. A method for using a wrist-worn nerve stimulator according to claim 7, comprising the following steps:

S1: finding the nerve in a wrist and marking a position for neurotherapy in an area of the wrist;

S2: measuring the distance between the marked position and the nerve in the area of the wrist, as well as the size of the wrist, to select an appropriate second strap;

S3: tearing the release film on a part of the hydrogel by hand to expose the hydrogel connected with conductive foam;

S4: fitting the hydrogel to a corresponding nerve position on the wrist part;

S5: tearing off the release film on the other part of the hydrogel, fitting the remaining hydrogel with the corresponding nerve, and ensuring that an electrode slice used to construct a circuit is pasted on the back of the wrist;

S6: sleeving the second strap onto the wrist, overlapping it onto the first strap, and adjusting the second strap to make the conduction plate overlapped with the conductive foam; and S7: adjusting the marking indicators on the second strap and the first strap to align them with each other, and after adjustment, activating the electrical stimulation part to start therapy.

* * * * *